United States Patent
Kaltenbacher et al.

(10) Patent No.: US 6,813,427 B1
(45) Date of Patent: Nov. 2, 2004

(54) FLUORESCENCE BASED LIQUID CORE WAVEGUIDE

(75) Inventors: Eric Kaltenbacher, St. Petersburg, FL (US); Lawrence C. Langebrake, Seminole, FL (US); Bob Byrne, St. Petersburg, FL (US); Robert Waterbury, Palm Harbor, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/869,653
(22) PCT Filed: Dec. 22, 1999
(86) PCT No.: PCT/US99/30774

§ 371 (c)(1),
(2), (4) Date: Feb. 15, 2002

(87) PCT Pub. No.: WO00/39615

PCT Pub. Date: Jul. 6, 2000

Related U.S. Application Data (60) Provisional application No. 60/114,212, filed on Dec. 29, 1998, and provisional application No. 60/114,354, filed on Dec. 29, 1998.

(51) Int. Cl.$^7$ ................................................ G02B 6/02
(52) U.S. Cl. .................. 385/125; 385/123; 356/300
(58) Field of Search ................................ 356/300–334, 356/246; 385/12, 31, 32, 33, 125

(56) References Cited

U.S. PATENT DOCUMENTS

| | | |
|---|---|---|
| 3,770,350 A | 11/1973 | Stone et al. |
| 4,852,666 A | 8/1989 | Brunet et al. |
| 5,412,750 A * | 5/1995 | Nath ........................ 385/125 |

(List continued on next page.)

FOREIGN PATENT DOCUMENTS

| DE | 35 29 488 A | 2/1987 |
|---|---|---|
| EP | A-0 708 323 | 4/1996 |

OTHER PUBLICATIONS

Lacki et al: 'Liquid Core Waveguide as a Fluorescence Sensor' Eurosensors. Proceedings of the European Conference on Solid–State Transducers and the UK Conference on Sensors and Their Applications, vol. 1, Sep. 13, 1988, pp. 343–346.

Altkorn R et al: 'Low–Loss Liquid–Core Optical Fiber for Low Refractive–Index Liquids: Fabrication, Characterization, and Application in Raman Spectroscopy' Applied Optics, Optical Society of America, Washington, US, vol. 36, No. 34, Dec. 1, 1997, pp. 8992–8998.

(List continued on next page.)

*Primary Examiner*—Akm Enayet Ullah
*Assistant Examiner*—Jennifer Doan
(74) *Attorney, Agent, or Firm*—Calfee, Halter & Griswold, LLP (57) ABSTRACT

A liquid core waveguide for fluorescence spectroscopy is provided. According to one version of the present invention, a substantially cylindrical support tube is provided, having a substantially constant outer diameter, and a flexible tube is wrapped in contiguous windings about the outer surface of the support tube to form a tight coil about the support tube which is configured of material that is transmissive of light in the relatively short wavelength range which is used to excite the molecular material in the flexible tube. This feature enables the flexible tube to be wound tightly about the support tube without crimping (thereby to form the liquid core waveguide into a compact package), and enables light in the relatively short excitation range to be effectively transmitted through the support tube and into the flexible tube.

20 Claims, 2 Drawing Sheets

U.S. PATENT DOCUMENTS

| | | | |
|---|---|---|---|
| 5,416,879 A | | 5/1995 | Liu |
| 5,596,671 A | * | 1/1997 | Rockwell, III .............. 385/147 |
| 5,604,587 A | | 2/1997 | Che et al. |
| 5,606,170 A | | 2/1997 | Saaski et al. |
| 5,680,209 A | | 10/1997 | Mächler |
| 6,011,882 A | * | 1/2000 | Dasgupta et al. ............. 385/12 |
| 6,016,372 A | | 1/2000 | Fein et al. |
| 6,108,083 A | * | 8/2000 | Machler ...................... 356/328 |
| 6,332,049 B1 | * | 12/2001 | Dasgupta ..................... 385/12 |
| 6,385,380 B1 | * | 5/2002 | Friedrich et al. ........... 385/125 |

OTHER PUBLICATIONS

Fujiwara K et al: 'Liquid Core Optical Fiber Total Reflection Cell as a Colorimetric Detector for Flow Injection Analysis' Analytical Chemistry, American Chemical Society. Columbus, US, vol. 57, No. 6, 1985, pp. 1012–1016.

Altkorn R et al: 'Waveguide Capillary Cell for Low–Refractive–Index Liquids' Applied Spectroscopy, The Society for Applied Spectroscopy, Baltimore, US, vol. 51, No. 10, Oct. 1, 1997, pp. 1554–1558.

Fujiwara et al., "Liquid Core Optical Fiber Total Reflection Cell as a Colorimetric Detector for Flow Injection Analysis," *Anal. Chem.*, vol. 57, No. 6 (May 1985), pp. 1012–1016.

Byrne et al., "Construction of a compact spectrofluorometer/ spectrophotometer system using a flexible liquid core waveguide," *Talanta 000* (1999) 000–000, pp. 1–6.

\* cited by examiner

FLUORESCENCE BASED LIQUID CORE WAVEGUIDE

This patent is based on an application which is a national phase entry under 35 U.S.C. §317, which claims priority to U.S. provisional application Nos. 60/114,212 and 60/114,354, both of which were filed Aug. 29, 1998, the disclosures of which are incorporated herein by reference.

GOVERNMENT SUPPORT

A portion of the work described herein was supported by the Office of Naval Research under Contract No. N0014-96-1-5011.

TECHNICAL FIELD

The present invention relates to a liquid core waveguide and particularly to a liquid core waveguide for fluorescence spectroscopy.

BACKGROUND

In earlier International Application PCT/US99/09395 (Publication No. WO 99/157584) entitled "Liquid Core Waveguide," there is disclosed a new and useful liquid core optical waveguide which is particularly suitable for long pathlength absorbance spectroscopy. The waveguide is formed from flexible tubing having a flexibility and structural integrity allowing it to be coiled into a small volume without crimping. By this means, waveguides having long optical pathlengths can be provided in very compact spaces.

SUMMARY OF THE PRESENT INVENTION

In accordance with the present invention, it has now been discovered that liquid core waveguides of the type described in the above-noted International Application PCT/US99/09395 and having long optical pathlengths in very compact spaces can also be made especially for use in emission spectroscopy such as fluorescence spectroscopy and the like.

In accordance with the present invention, a liquid core waveguide (LCW) comprises a flexible tube providing a liquid core and a light coupling for at least one end of the flexible tube. The flexible tube (i) has a substantially circular cross section and a substantially constant diameter, (ii) an index of refraction less than the index of refraction of a liquid which is disposed in the flexible tube, and (iii) is made from a material such that a cylindrical tube made from such material and having a liquid core diameter of about 560 $\mu$m. an outer diameter of about 800 $\mu$m and a length of about 5 meters can be coiled within a volume space of about 1.57 cubic inches and support a body of aqueous medium over its length without crimping.

A liquid core waveguide device for fluorescence spectroscopy, according to one preferred version of the present invention, includes a liquid core comprising a flexible tube which is configured into a coil, and is transmissive to light in relatively short wavelengths (e.g. ultraviolet light). The flexible tube has at least one light outlet (or "light coupling device") through which longer wavelength light (e.g. visible light) can pass. A light source is disposed at least partially within the coil and is configured to direct light of a relatively short wavelength range into the flexible tube to excite molecular material in the liquid core. The flexible tube is configured to contain a portion of light emissions of a longer wavelength (e.g. visible light) from the excited molecular material in the liquid core and to direct such portion of longer wavelength light emissions toward the light outlet.

According to one version of the present invention, the flexible tube has a plurality of light outlets, each configured to transmit longer wavelength light emissions. Moreover, the flexible tube is configured to direct the portion of the light emissions toward each of said plurality of light outlets, and a light coupler is provided in communication with each of the plurality of light outlets. The light coupler is configured to couple the light emissions from the plurality of light outlets and to direct the coupled light emissions from the plurality of light outlets to a spectrophotometric device for analyzing such light emissions.

In another preferred version of the present invention each of the plurality of light outlets has a coupling device with a graded index (GRIN) lens for providing a predetermined profile to the light emissions exiting from each respective light outlet. Moreover, the flexible tube has a liquid core with a substantially constant cross section circular inner diameter, the GRIN lens at each light outlet has a cylindrical profile with a circular cross sectional diameter which is greater than the circular cross sectional diameter of the flexible tube, and the GRIN lens at each light outlet is substantially coaxial with its respective light outlet. Thus, a substantial portion of the light emissions passing through such light outlet is captured by the GRIN lens associated with the light outlet.

Still further, according to another feature of the present invention, a substantially cylindrical support tube is provided, having a substantially constant outer diameter, and the flexible tube is wrapped in contiguous windings about the outer surface of the support tube to form a tight coil about the support tube. The light source is disposed at least partially within the support tube, and the support tube is configured of material that is transmissive of light in the relatively short wavelength range which is used to excite the molecular material in tile flexible tube. This feature enables the flexible tube to be wound tightly about the support tube without crimping (thereby to form the liquid core waveguide into a compact package), and enables light in the relatively short excitation wavelength range to be effectively) transmitted through the support tube and into the flexible tube.

In yet another aspect of the present invention, the light source is configured to allow selective control the wavelength of the ultraviolet light (or other light suitable to cause fluorescence) that is transmitted into the flexible tube. For example, the light source can comprise a light emitter (e.g. broadband or ultraviolet), and a light filter can be provided between the light emitter and the support tube, for controlling the wavelength range of light from the light emitter that is directed into the support tube. The light filter is moveable relative to the light source and the flexible tube, and includes a plurality of narrow band filters which enable selective control of the wavelength range of light within the excitation range which is transmitted from the light emitter to the flexible tube.

In still another aspect of the present invention, a liquid core waveguide capable of being used for both fluorescence spectroscopy and absorbance spectroscopy is provided. In this embodiment, flexible tubing transmissive to ultraviolet light is arranged about an ultraviolet light source in the same way as described above in connection with the other embodiments of the invention. However, in this embodiment, a tight source useful for absorbance spectroscopy (e.g. a source of visible light) is optically coupled to the connector at one end of the flexible tubing. When this device is used for fluorescence spectroscopy, it operates in much the same way as the other embodiments of this invention as described above in that light from the ultraviolet light source is transmitted into the flexible tubing and the fluorescence caused thereby is transmitted through the connector located at tile other end of the flexible tubing for detection by a spectrometer attached thereto. In this mode of operation, the source of visible light is inactive. However, when this device is used for absorbance spectroscopy, the operation of the lights is reversed—i.e., the visible light source is turned on while the ultraviolet light source is turned off. Accordingly, in this mode of operation, visible light is transmitted through the coupling on one end of the flexible tubing into the liquid core therein and attenuated light is transmitted through the coupling on the other end of the flexible tubing for detection by the spectrometer optically coupled thereto in a manner like that occurring with the wave guides shown in International Application PCT/US99/09395. In both modes of operation, measurements of high sensitivity can be obtained with a very compact system.

When operated in the fluorescence mode, the light source of the inventive wave guide is preferably an ultraviolet source, and the support tube is formed of quartz or another material which is substantially transmissive to light in the ultra violet range. Moreover, the flexible tube is preferably formed of Teflon® AF-2400 or other material that is substantially transmissive to light in the ultra violet range. Most preferably, the flexible tube is made from a material such as Teflon® AF-2400 which is substantially transmissive to ultra violet light and which also has an index of refraction less than that of water.

In an optional embodiment of the invention, the coupling devices through which liquid is directed into and out of the flexible tube, and through which light emissions are directed out of the flexible tube, are preferably formed with a graded index (GRIN) lens according to the principles described in commonly assigned U.S. Provisional Application Ser. No. 60/114,212, entitled *Coupling Device For Liquid Core Waveguide*, the disclosure of which is incorporated herein by reference. In this embodiment, each coupling device comprises a housing supporting a fluid connector, a light connector and a tube connector. Tile fluid connector is configured for attachment to a fluid conduit for directing liquid into or out of the tube. The light connector is configured for connection to a light conduit such as a light fiber for directing light to an analytical device such as a spectrometer. The tube connector is configured for connection to an end of the flexible tube, and a graded index (GRIN) lens is provided between the light connector and the tube connector to substantially focus light transmitted between the light connector and the flexible tube. The GRIN lens has a substantially cylindrical configuration, is supported in the coupling device in a co-axial relationship with the portion of the flexible tube disposed within the tube connector, and has a cross sectional area which is larger than the cross sectional area of the portion of the flexible tube disposed within tile tube connector, whereby the GRIN lens, when disposed to transmit light passing from the portion of flexible tube to a light conduit is oriented to capture substantially all of the light passing through the outlet of the flexible tube.

A liquid core waveguide device according to this form of the present invention is particularly configured for fluorescence spectroscopy, and comprises a flexible tube of the type described above, in a length of no more than 2 meters, coiled tightly about a quartz cylinder. An ultra violet light emitter is disposed within the cylinder, and is oriented to direct ultra violet light outward and through the cylinder and flexible tube, to excite molecular material within the flexible tube. In accordance with known fluorescence principles, the molecular material fluoresces, emits light in the visible range, and a substantial portion of that emitted visible light is retained in the flexible tube and directed by the flexible tube toward one or more light connectors, each of which is supported by a coupling device of the type described above. In each coupling device, substantially all of the emitted visible light is captured and focused by the GRIN lens, and directed to a light fiber (or fibers) which in turn transmit it to an analytical device.

A fluorescence based liquid core waveguide, which selectively controls the bandwidth of the ultraviolet light directly into the flexible tube, according to a specific aspect of the present invention, is intended to be particularly versatile, in the sense that it provides for selective examination and analysis of liquid samples under a number of selectively chosen light excitation sources and with a variety of materials in the liquid disposed in the flexible tube.

Further features of the present invention will become further apparent from the following detailed description and the accompanying drawings.

DETAILED DESCRIPTION

Fluorescence Based Spectroscopy

As described above, the present invention relates to a liquid core waveguide device which is particularly useful in fluorescence spectroscopy, and whose principles may also be useful in other applications, e.g. other types of emission based spectroscopy. The present invention is described herein in a system for fluorescence spectroscopy.

Fluorescence based spectroscopy, as used herein, is intended to mean a system in which light having a relatively short wavelength (e.g. ultra violet light) excites molecular material in a liquid sample, and the excited molecular material emits light in a relatively longer wavelength (e.g. in the visible range). The principles of the invention are described herein in a system which utilizes an ultra violet light source and in which light in the visible range is emitted from the excited molecular material in the liquid sample. However, it will be clear to those skilled in the art that the principles of this invention can be utilized in a system with other forms of light source and with emitted light in a different wavelength range, so long as the system operates on the fluorescence principles described herein.

Figure 1:
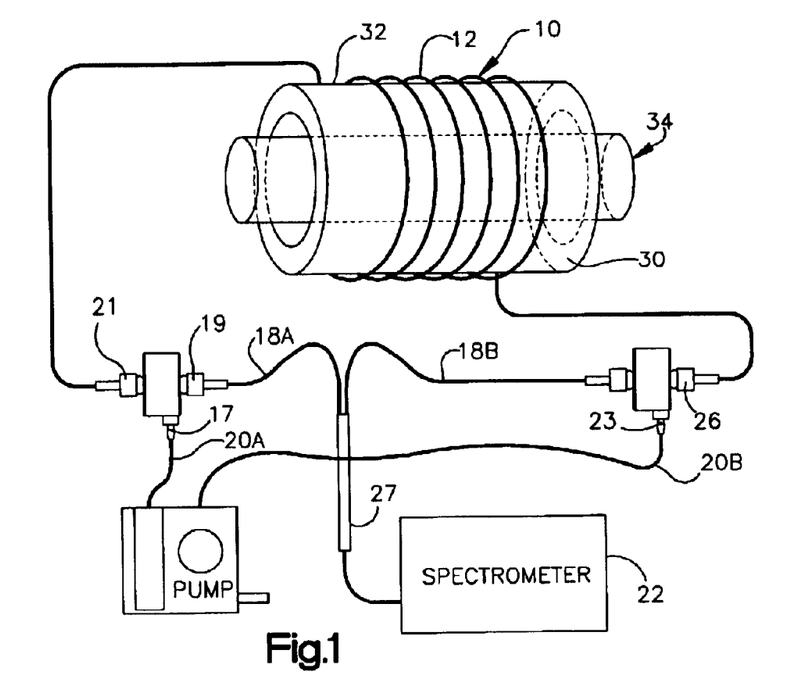
FIG. 1 is a schematic illustration of a liquid core waveguide system for fluorescence spectroscopy, according to the present invention.
Figure 2:
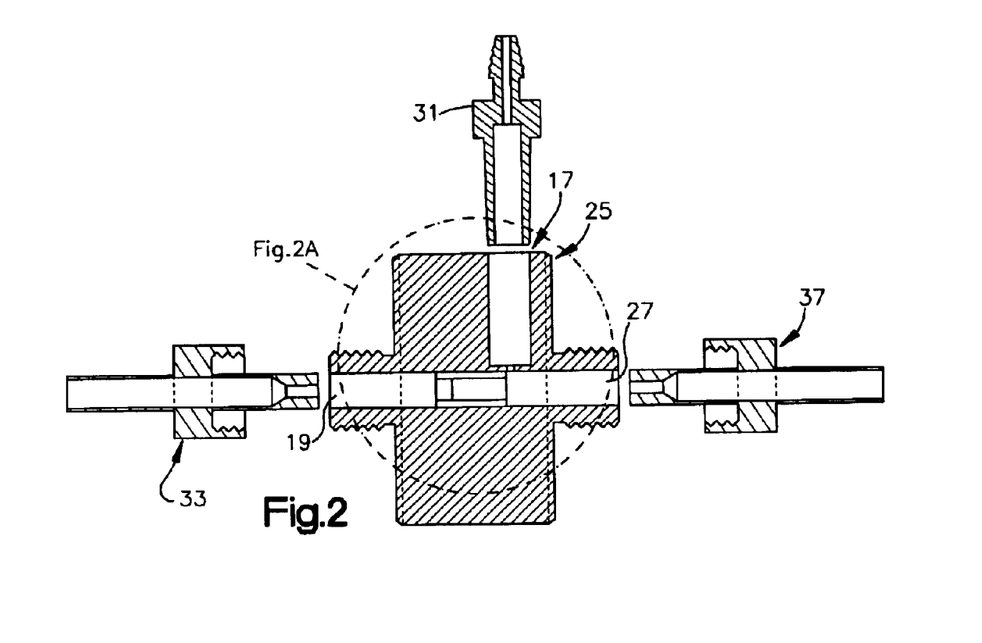
FIG. 2 is a partially exploded cross sectional view of a coupling device for use with a waveguide according to the present invention taken from the direction A—A of FIG. 2-B.
Figures 2A, 2B, 2C:
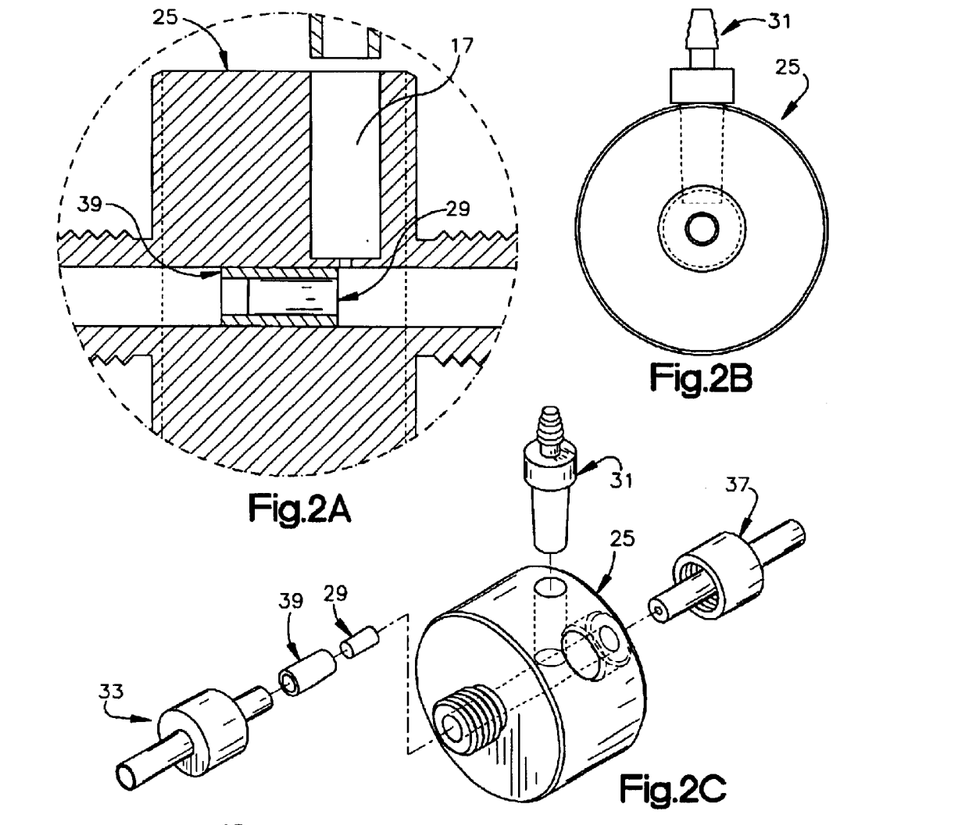
FIG. 2A is an enlarged, fragmentary view of the area A-2 of FIG. 2.
FIG. 2B is an end view of one of the coupling devices of the system of FIG. 1, the other couplings device being similarly configured.
FIG. 2C is a three-dimensional, partially exploded view of the coupling device of FIGS. 2, 2A and 2B.

A system for fluorescence spectroscopy is illustrated in FIG. 1. The system includes a liquid core waveguide 10 including a flexible tube 12 made of Teflon® AF-2400 (e.g. from Biogeneral), with an inner diameter of about to 560 μm and an outer diameter of about to 800 μm. A length of liquid the flexible tube 12, e.g. not exceeding 2 meters in length, is coiled about a cylindrical support tube 30 and placed in a chamber (not shown) which is configured to prevent ambient light coupling into the liquid core waveguide. Coupling devices, 16,26, each of which is configured according to Exhibit A, and described further below, is provided at each end of the tube 12. The coupling devices enable liquid samples to be directed into and out of the flexible tube, and are also designed to interface the liquid core waveguide 10 to light conduits comprising optical fibers 18A. 18B (e.g. Polymicro Technologies 150 μm core diameter), and liquid conduits 20A, 20B, each comprising a standard 5 mm ID silicon tube. One coupling device 16 provides a liquid connector 17 through which liquid is directed into the tube 12 (see FIG. 2-A), a light connector 19, and a tube connector 21 for one end of the tube 12. The light connector 19 and the tube connector 21 are configured such that visible light from the tube 12 is directed to the optical fiber 18A through which visible light emissions from the tube 12 are directed to a spectrometer 22 (via a light coupler 27). A second coupling device 26 is disposed at the other end of the tube 12. The coupling 26 is similar to the coupling device 16 and includes a liquid connector 23 through which liquid is directed out of the tube 12, and a light connector 25 through which visible light from the other end of the tube 12 is directed to optical fiber 18B, for transmitting visible light emissions from the tube 12 to the spectrometer 22 (also via the light coupler 27). The tube 12 has a substantially constant cross section over its entire length.

Also, flexible tube 12 has a substantially cylindrical configuration over its length. Thus, the liquid core has a substantially circular cross section with an inner diameter which, in the preferred embodiment is preferably about 560 μm and an outer diameter which, in the preferred embodiment is about 800 μm. Thus, the preferred wall thickness of the tube 12 is about 120 μm, and it is believed that the wall thickness of a length of tubing according to the preferred embodiment would be at least about 100 μm.

In the embodiment of FIG. 1, the Teflon® AF 2400 flexible tube 12 is wound about the substantially cylindrical support tube 30, which is preferably made of quartz of other material which is transmissive to ultra violet light. The support tube 30 has a substantially smooth cylindrical outer surface 32, which enables the flexible tube 12 to be wound into tight contiguous windings about the support tube 30. This enables the flexible tube 12 to be formed into a relatively tight, compact package, without crimping.

Further, in the embodiment of FIG. 1, an excitation light source, e.g. an ultra violet (UV) light source 34, is disposed within the cylindrical support tube 30. The UV light source 34 directs UV light radially outward, through the quartz tube 30 and the flexible tube 12, and into the liquid sample within the flexible tube 12. That UV light excites molecular material in the liquid sample causing the excited molecular material to fluoresce and emit light in a relatively longer wavelength (e.g. in this case to emit light in the visible range). A significant portion of such emitted light is confined within the flexible tube 12 and is directed toward the coupling devices 16,26 at the ends of the flexible tube 12. Further, in accordance with the invention, such visible light is captured and focused by a GRIN lens 29 in each coupling device (see FIGS. 2, 2A, 2B and 2C further described below) and directed to a respective optical fiber 18A, 18B. Still further, the emitted light conducted by the silicon light tubes 18A, 18B are combined (i.e. coupled) by the fiber splitter 27, and directed to an analytical light device such as the spectrometer 22.

According to another aspect of the present invention, the bandwidth of the UV light directed into the flexible tube 12 can be selectively controlled. Specifically, referring to FIG. 3, a broadband (masked) UV light source 40 is disposed within a banded (prism shaped) interference filter 42. Both of these elements are disposed within a quartz support tube 44 and the flexible tube 12 is wound tightly in contiguous windings about the support tube 44. An outer reflective shield 46 can surround the support tube 44 and the windings of flexible tube 12. The outer reflective shield 46 reflects any UV light passing beyond the coils of the flexible tube back into the tube 12. With this embodiment, the interference filter 42 is moveable axially relative to the UV light source 40 and the support tube 44. As the filter 42 moves, it selectively controls the wavelength range of UV light which is transmitted to the flexible tube 12. This feature enables the system to be particularly versatile, in its ability to provide different types of analysis of different types of molecular materials in a liquid sample within the flexible tube.

Figure 3:
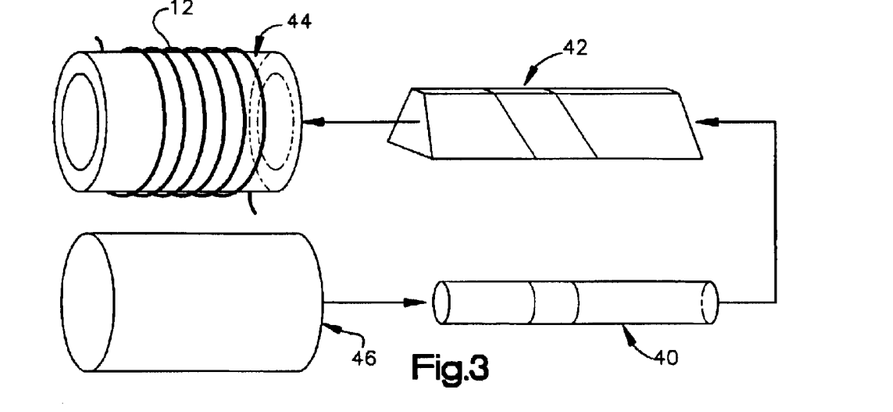
FIG. 3 is a schematic illustration of a liquid core waveguide system, useful for fluorescence spectroscopy according to the present invention, and configured to control the band width of excitation light directed into the waveguide.

Moreover, it is contemplated that the UV light source could be located outside the quartz support tube 44, and direct UV light emissions into the support tube 44, and a reflector inside the support tube 44 would reflect such UV light emissions radially outward through the quartz support tube 44 and into the flexible tube 12. In such a system, an interference filter similar to the filter 42 could be disposed between the reflector and tie support tube, or outside the support tube and between the light source and the reflector. In this application, reference to a light source being located at least partially within the coiled flexible tube is intended to encompass all of the foregoing embodiments.

Accordingly, there is described above in a liquid core waveguide system for fluorescence based spectroscopy. Fluorescence based spectroscopy, as used herein, is intended to mean a system in which light having a relatively short wavelength (e.g. ultra violet light) excites molecular material in a liquid sample, and the excited molecular material fluoresces and emits light in a relatively longer wavelength (e.g. in the visible range). The principles of the invention are described herein in a system which utilizes an ultra violet light source and in which light in the visible range is emitted from the excited molecular material in the liquid sample. However, it will be clear to those skilled in the art that the principles of this aspect of the invention can be utilized in a system with other forms of light source and with emitted light in a different wavelength range, so long as the system operates on the fluorescence principles described herein.

Optional Coupling Device

A coupling device that may be used for optically coupling the end of the flexible tubing used in wave guides of the present invention (whether in the fluorescence or absorbance modes) to a light source or detection device is schematically illustrated in FIGS. 2, 2A, 2B and 2C. As shown in these figures, coupling device 16 comprises a housing 25 preferably formed of Delrin® (DuPont) and has the liquid port 17, the light port 19 and a tube connector port 27 formed therein. The liquid port 17 is configured for attachment to a fluid connector 31 which in turn is adapted for connection to a fluid conduit (e.g. silicon tubing 20) for directing liquid into or out of the tube 12. The light port 19 is configured for connection to a light connector 33. The light connector 33 is configured to support a light conduit comprising one or more light fibers 18A connected to the light source. The tube connector port 27 is configured for connection to a tube connector 37 which, in turn, supports an end of the flexible tube 12. A graded index cylindrical (GRIN) lens 29 is disposed within a sheath 39 located in the housing 25. The liquid port 17 directs liquid into the coupling device at a location between the GRIN lens 29 and the tube connector 37 (see FIG. 2A). Thus, the GRIN lens does not affect liquid flow into or out of the tube 12. The GRIN lens 29 functions to substantially focus light transmitted into the housing 25 through the light fiber(s) 18A and to direct the focused light into the flexible tube 12. In one embodiment GRIN lens 29 functions to collimate light transmitted into the housing 25 through the light fiber(s) 18A and to direct the collimated light into the flexible tube 12.

According to the preferred form of the present invention, the GRIN lens 29 and the end of the flexible tube are held in substantially fixed, coaxial relation to each other within the housing 25. The sheath 39 is configured for a tight fit with the interior wall of the housing, and the GRIN lens has a tight fit with the sheath 39, to maintain the GRIN lens 29 in fixed position in the housing 25. The tube connector port 27 tightly supports the tube connector 37 (e.g. by a threaded connection) and the tube connector 37 has an axial passage which tightly supports the end of the tube 12 in fixed coaxial relation to the GRIN lens 29. Moreover, the light connector 33 is tightly supported in the light port 19 (e.g. by a threaded connection), and the light connector 33 has an axial passageway which in turn tightly supports the light fiber(s) 18A in position in the light port 19. The cross section of the GRIN lens is substantially larger than the cross section of the light fiber(s) supported by the light connector 33, and the GRIN lens is located to extend across and radially beyond the light fiber(s) such that substantially all of the light transmitted through the light fibers(s) 18A is captured and focused by the GRIN lens. In the disclosed embodiment, the fluid connector 31 is a nose barb (Cole Palmer Part No. FK-06359-17), each of the light and tube connectors 33, 37 is an SMA connector (Amphenol Part No. 905-150-XXXX), and the GRIN lens 29 is a Melles Griot Part No. 06LGE114.

Similarly, the coupling device 26 at the outlet side of the flexible tube is configured such that its GRIN lens has a substantially cylindrical configuration, is supported in the coupling device 26 in a co-axial relationship with the portion of the flexible tube disposed within the coupling device, and has a cross sectional area which is larger than the cross sectional area of the portion of the flexible tube disposed within the coupling device, whereby the GRIN lens in the coupling device 26 is designed to capture and focus substantially all of the attenuated light exiting the flexible tube and to direct that attenuated light to the light fiber(s) which transmit the attenuated light to a light conduit (e.g. a light fiber 18B) for directing the attenuated light to an analytical device such as the spectrometer 22.

The coupling device 25 is preferably formed of a Delrin® material, and the flexible tube 12 is preferably formed from a material whose index of refraction is less than that of water such as Teflon® AF-2400 material.

Absorbance Spectroscopy Using a GRIN Lens

In one embodiment of the invention, a liquid core waveguide particularly configured for absorbance spectroscopy comprises a relatively long flexible tube as described above, with each end of the tube being provided with a coupling device having a GRIN lens as also described above. The coupling device at one end of the tube is configured to direct liquid from a pump such as shown in FIG. 1 into the flexible tube and the coupling device at the other end of the flexible tube is configured to direct liquid from the liquid core. Further, the coupling device at the one end of the flexible tube is configured such that electromagnetic radiation from a broadband light source can be directed into the tube and attenuated light can be directed from the other end of the flexible attenuated light receiver to an analytical device such as a spectrometer.

For absorbance spectroscopy, liquid core waveguide device would be designed with the flexible tube having a length of at least 20 cm, and preferably several meters (e.g. 5–10 meters) between its ends. Additionally, the flexible tube has a wall thickness of at least 100 $\mu$m, and a ratio of length to liquid core volume that is greater than 300 cm/cm$^3$. Moreover, the GRIN lens has a length of about 5.4 mm., and a cross sectional diameter of about 1.8 mm., the light fiber(s) 18A and the flexible tube have cross-sectional diameters of less than the GRIN lens (e.g. the light fibers 18A including cladding have a cross sectional diameter of about 485 $\mu$m, and the flexible tube inner diameter is about 560 $\mu$m.

Sample solutions enter and exit the liquid core waveguide 10 through the liquid port 17 in the coupling device. A fiber-coupled light source 24 and a CCD array spectrometer 22 (e.g. Ocean Optics LS-1 Tungsten Halogen lamp and Ocean Optics S1000-TR-1 CCD array spectrometer) provide a broadband light source and spectral absorbance measurements, respectively, continuous sampling is achieved with a peristaltic pump 28(e.g. Ismatec, model 78016-30) at a flow rate of at least about 0.5 cm$^3$/min. In order to avoid formation of bubbles in the system the pump 28 is active only during periods of sample introduction. Continuous pumping of sample however, easily flushes out bubbles inadvertently introduced to the system.

In order to perform absorbance spectroscopy, reagent(s) and sample(s) are combined to produce colored species that are introduced into the liquid core waveguide. Reagents are generally analytical-reagent grade. As an example, for analysis of Ferrous ion, ferrozine (Sigma) reagent can be used as a colorimetric reagent. Moreover, buffer solutions, (pH=5.5) can be used to optimize color development. Absorbance measurements of each sample can be made relative to a reference solution containing no ferrozine reagent but identical to the sample solution in all other respects. Alternatively, reference solutions can be constituted from natural solutions that have had all iron removed using ion exchange resins. The absorbance peak of the Fe(II)-ferrozine complex (Fe(FZ)$_3$) at 562 nm (nanometers) can be used for the determination of Fe(II) concentration. The Fe(FZ)$_3$ absorbance maximum coincides with water's transmission window (480–700 nm), thus minimizing the extent of light absorption by water. Absorbances are referenced to a non-absorbing wavelength (700 nm) in order to compensate for instrumental drift. Analysis of aqueous solutions for total dissolved iron (Fe(III)+Fe(II)), rather than Fe(II) alone, can be accomplished by including a reductant (such as hydroxylamine hydrochloride) in the mixed buffer solution.

The sample size requirement for liquid core waveguide analysis is very low. For example, analysis with a 4 meter liquid core waveguide having a liquid core diameter of about 560 $\mu$m requires a sample size of less than 1.0 cm$^3$. The practical upper limit pathlength for liquid core waveguide analysis appears to be substantially larger than 4 meters (i.e. 10–20 meters). Light throughput is not a limiting analytical parameter for pathlengths of this magnitude. Flow throughput with a 5 meter liquid core waveguide with a diameter of about 560 $\mu$m is about 2 minutes.

Moreover, a cylindrical Teflon® AF 2400 tube with a 560 µm inner diameter and 800 µm outer diameter, and a length of at least 5 m can be entwined within a volume space of 1.57 cubic inches and support an aqueous core over it's length without crimping. "Entwined" is used to mean bent around multiple times in any manner, such as by way of example tightly coiled (little or no space between adjacent lengths), loosely coiled (more space between adjacent lengths), wound (as in thread wound around a spool or a length of rope wound), entwined in the ordinary sense (as in yarn entwined to form a ball of yarn), and haphazardly gathered into a "rats' nest." Thus, a long pathlength waveguide having the foregoing construction, can be housed in a relatively small volume space.

One of the most significant advantages of liquid core waveguide absorbance spectroscopic iron analysis, using a waveguide according to the present invention, is its substantial simplicity. Only one step, addition of combined reagent to a sample, is prerequisite to absorbance measurement. The absence of preconcentration steps considerably lessens the potential for sample contamination. Thus, very low (sub nanomolar) irons concentrations can be measured with this technique.

Moreover, a liquid core waveguide having a length of about 4 meters, and an inner diameter of about 560 µm, has an internal volume of less than 1 cm$^3$ and a length to volume ratio of at least 400 cm/cm$^3$. Thus, the length of tubing preferably has a ratio of length to liquid core volume that is ideally greater than 400 cm/cm$^3$ but given manufacturing tolerances, as a practical matter a ratio of length to liquid core volume that is greater than 300 cm/cm$^3$ is believed to be useful for practicing absorbance spectroscopy with a system according to the principles of the present invention. In any event, it should be clear that relatively small sample sizes are required for conducting long pathlength absorbance spectroscopy according to the principles of the present invention.

The principles of the present invention can be used to markedly extend the detection capabilities of many existing solution-based measurements obtained via absorbance spectroscopy. The analytical apparatus required for this analysis is very simple and robust. The overall analysis is quite amenable to miniaturization and autonomous in-situ analysis.

Fluorescence and Absorbance Spectroscopy Combined in Same Device

In still another aspect of the present invention, a liquid core waveguide capable of being used for both fluorescence spectroscopy and absorbance spectroscopy is provided. This device has a structure essentially the same as the device illustrated in FIG. 1. except that the distal end of optical fiber 18A, rather than being connected to spectrometer 22 as shown in FIG. 1, is connected to a source of broadband radiation such as a visible light source (not shown).

When this device is used for fluorescence spectroscopy, it operates in essentially the same way as the embodiment of FIG. 1 in that light from ultraviolet light source 34 is transmitted into flexible tubing 12 and the fluorescence caused thereby is transmitted through the coupling device 26 located at the outlet end of the flexible tubing and through optical fiber 18B for detection by spectrometer 22. In this mode of operation, the source of visible light is inactive. However, when this device is used for absorbance spectroscopy, the operation of the lights is reversed—i.e., the visible light source (not shown) is turned on while the ultraviolet light source is turned off. Accordingly, in this mode the device operates in a manner similar to the device of International Application PCT/US99/09395 in that broadband light (e.g. visible light) from the light source is transmitted through optical fiber 18A and coupling device 19 into the liquid being analyzed in flexible tubing 12, while attenuated light produced inside flexible tube 12 is then transmitted through coupling device 26 and optical fiber 18B for detection by spectrometer 22. In both modes of operation, measurements of high sensitivity can be obtained with a very compact system. Nonetheless, both modes of operation, fluorescence and absorbance, are combined in a single device. This provides an especially attractive combination of simplicity, versatility, compactness and accuracy in an important analytical tool widely used in science and industry.

The Flexible Tubing

It should be noted that it is useful to describe the flexibility and structural integrity of a length of tubing forming a liquid core waveguide according to the invention by referring to certain parameters of the preferred embodiment (i.e. that a length of tubing having, a length of about 5 meters, a liquid core cross section diameter of about 560 µm, and an outer diameter of about 800 µm could be entwined in a volume space of about 1.57 cu. in. and support an aqueous medium over its length without crimping). However, such a parametric description of the tubing is believed to be useful in describing the type of tubing, in terms of flexibility and integrity with which the present invention can be implemented, but is not intended to limit the invention to tubing of those exact dimensions, other than may be recited in specific claims of this application. For example, tubes having cores 200 µm to 1 mm in diameter and outer diameters of 500 µm to 2 mm are also useful in accordance with the present provided they also have qualities of flexibility and integrity allowing entwinement of a 5 meter length of the tube in a small space without crimping as described above.

In addition, while the invention has been described above in terms of lengths of tubing in the range of 4 meters, 5–10 meters and longer, it is also contemplated that long pathlength absorbance spectroscopy can be practiced effectively with liquid core waveguides as short as 20 cm, and 1 meter in length, and also with liquid core waveguides on the order of several meters, 5–10 meters, and longer, using the principles of the present invention.

What is claimed is:

1. A liquid core waveguide device for fluorescence spectroscopy, comprising
    a) a flexible tube for defining a liquid core and being transmissive to light in a relatively short excitation wavelength range, the flexible tube being configured into a coil and having at least one outlet end,
    b) a light coupling device connected to the outlet end of the flexible tube through which emitted light in a relatively longer wavelength range can pass, and
    c) a first light source configured to direct light in the relatively short excitation wavelength range through the walls and into the liquid core of the flexible tube to excite molecular material in the core, wherein at least a portion of the first excitation light source is arranged in the coil.

2. The liquid core wave guide of claim 1, wherein the first light source is capable of generating ultraviolet light of a wavelength suitable to cause fluorescence of a material in the liquid core.

3. The liquid core waveguide of claim 1, further comprising a support tube, the flexible tube being wrapped in windings about the outer surface of the support tube to form a tight coil about the support tube, wherein the light source is disposed at least partially within the support tube, and wherein the support tube is configured of material which is transmissive of light in the relatively shorter excitation wavelength range.

4. The liquid core waveguide of claim 3, including a filter device configured to selectively control the wavelength range of the relatively shorter wavelength excitation light which is transmitted into the flexible tube.

5. The liquid core waveguide of claim 4, wherein the filter is disposed between the first light source and the flexible tube, and the filter includes a plurality of narrow band filters which enable selective control of the wavelength range of light within the excitation range which is transmitted from the light source to the flexible tube.

6. The liquid core waveguide of claim 4, wherein the filter is disposed between the first light source and the flexible tube, and the filter is moveable relative to the support tube.

7. The liquid core waveguide of claim 3, wherein the first light source comprises a light emitter disposed outside of the support tube and disposed to direct light in the excitation range into the support tube, and further wherein a reflector is provided within the support tube for redirecting light from the emitter toward the flexible tube.

8. The liquid core waveguide of claim 1,
wherein both ends of the flexible tube are provided with light coupling devices, each configured to enable light emissions to pass there through,
wherein the flexible tube is configured to direct a portion of the light emissions toward each light coupling device, and
wherein a light splitter is provided in communication with each light coupling device, the light splitter being configured to couple the light emissions from the light coupling devices on both ends of the tube and to direct the coupled light emissions to a spectophotometric device for analyzing such light emissions.

9. A liquid core waveguide device for fluorescence spectroscopy, comprising
a) a flexible tube for defining a liquid core and being transmissive to light in a relatively short excitation wavelength range, the flexible tube having at least one outlet end,
b) a light coupling device connected to the outlet end of the flexible tube through which emitted light in a relatively longer wavelength range can pass, wherein each light coupling device has a graded index (GRIN) lens for providing a predetermined profile to the light passing therethrough, and
c) a first light source configured to direct light in the relatively short excitation wavelength range through the walls and into the liquid core of the flexible tube to excite molecular material in the core.

10. The liquid core waveguide of claim 9, wherein the flexible tube has a core with substantially constant cross section circular inner diameter, the GRIN lens at each light coupling device having a cylindrical profile with a circular cross sectional diameter which is greater thin the circular cross sectional diameter of the flexible tube, and wherein the GRIN lens at each light coupling device is substantially coaxial with its respective light coupling device, whereby a substantial portion of the light emissions passing through the light coupling device is captured by the GRIN lens associated with the light coupling device and directed to the light coupler.

11. A liquid core waveguide device for fluorescence spectroscopy, comprising
a) a flexible tube for defining a liquid core and being transmissive to light in a relatively short excitation wavelength range, the flexible tube having at least one outlet end,
b) a light coupling device connected to the outlet end of the flexible tube through which emitted light in a relatively longer wavelength range can pass, wherein both ends of the flexible tube are provided with a light coupling device through which emitted light in a relatively longer wavelength range can pass, and
c) a first light source configured to direct light in the relatively short excitation wavelength range through the walls and into the liquid core of the flexible tube to excite molecular material in the core,
the waveguide further comprising a second light source capable of generating broadband electromagnetic radiation, the second light source being optically connected to the light coupling device on the end of the flexible tube opposite the outlet end whereby light from the second light source can be directed into the core of the flexible tube and attenuated light produced in the core can be directed through the outlet end of the flexible tube for analysis.

12. The liquid core wave guide of claim 11, wherein the flexible tube is configured into a coil and wherein at least a portion of the first excitation light source is arranged in the coil.

13. The liquid core wave guide of claim 12, wherein the first light source is capable of generating ultraviolet light of a wavelength suitable to cause fluorescence of a material in the liquid core.

14. The liquid core waveguide of claim 13, further comprising a support tube, the flexible tube being wrapped in windings about the outer surface of the support tube to form a tight coil about the support tube, wherein the light source is disposed at least partially within the support tube, and wherein the support tube is configured of material which is transmissive of light in the relatively shorter excitation wavelength range.

15. The liquid core waveguide of claim 11, wherein the first and second light sources can be individually activated whereby the waveguide can be used for fluorescence spectroscopy by activating the first light source and deactivating the second light source and, in addition, be used for absorbance spectroscopy by activating the second light source and deactivating the first light source.

16. A liquid core waveguide system comprising a flexible tube and a coupling device providing a liquid and a light coupling for at least one end of said flexible tube, said flexible tube (i) having a substantially circular cross section and a substantially constant diameter, and (ii) having an index of refraction less than the index of refraction of a liquid which is disposed in the flexible tube, the coupling device comprising a housing and a graded index (GRIN) lens to substantially focus light transmitted to a light conduit spaced from the flexible tube.

17. The liquid core waveguide of claim 16, wherein the flexible tube is configured into a coil, and wherein the GRIN lens and the end of the flexible tube are hold in substantially fixed, coaxial relation to each other within the coupling device.

18. The liquid core waveguide of claim 17, wherein a portion of the flexible tube is disposed with the coupling device and further wherein the GRIN lens has a substantially cylindrical configuration and a cross-sectional area which is larger than the cross-sectional area of the portion of the flexible tube disposed within the coupling device, whereby the GRIN lens is oriented to capture substantially all of the light passing through the coupling device.

19. The liquid core waveguide of claim 18, wherein the coupling device defines a fluid port, a light port and a tube connector formed therein, the fluid port configured for attachment to a fluid conduit, the light port being configured for connection to a light conduit, and the tube connector being configured for connection to an end of the flexible tube, and wherein the light port includes the graded index (GRIN) lens.

20. The liquid core waveguide of claim 19, wherein a light connector is disposed in the light port and a tube connector is disposed in the tube connector port of the coupling device, a light conduit comprising one or more light fibers being disposed within the light connector and the portion of the flexible tube being disposed within the tube connector, the light and tube connectors being configured to hold the light conduit and tube in relatively fixed position with the coupling device, and the GRIN lens being disposed within a supporting sheath located in a passageway disposed in the coupling device and located between the light and tube connectors, the fluid port being disposed to communicate liquid between the light port and the tube connector port at a location disposed between the GRIN lens and the tube connector port.

* * * * *